(12) United States Patent
Adams

(10) Patent No.: US 9,663,691 B2
(45) Date of Patent: May 30, 2017

(54) PRODUCTION OF HIGHLY IONIZED ALKALINE WATER USING A COMBINATION OF REDUCING METALS AND REDUCTIVE MINERALS

(71) Applicant: Electrolyzed Innovations, LLC, Piqua, OH (US)

(72) Inventor: Philip Adams, Piqua, OH (US)

(73) Assignee: Electrolyzed Innovations, LLC, Piqua, OH (US)

( * ) Notice: Subject to any disclaimer, the term of this patent is extended or adjusted under 35 U.S.C. 154(b) by 47 days.

(21) Appl. No.: 14/627,313

(22) Filed: Feb. 20, 2015

(65) Prior Publication Data

US 2016/0244648 A1    Aug. 25, 2016

(51) Int. Cl.

| | |
|---|---|
| A61K 33/06 | (2006.01) |
| A23L 33/16 | (2016.01) |
| C09K 3/00 | (2006.01) |
| A23F 5/00 | (2006.01) |
| A23L 2/38 | (2006.01) |
| A61K 33/00 | (2006.01) |
| B01J 8/02 | (2006.01) |
| C02F 1/70 | (2006.01) |
| C11D 3/04 | (2006.01) |
| A23L 2/52 | (2006.01) |
| C11D 3/00 | (2006.01) |
| A61K 45/06 | (2006.01) |
| A61K 33/08 | (2006.01) |
| A61K 33/24 | (2006.01) |
| A61K 33/26 | (2006.01) |
| A61K 33/30 | (2006.01) |
| A61K 33/34 | (2006.01) |
| A23K 50/48 | (2016.01) |
| C02F 103/02 | (2006.01) |

(52) U.S. Cl.
CPC .............. *C09K 3/00* (2013.01); *A23F 5/00* (2013.01); *A23K 50/48* (2016.05); *A23L 2/38* (2013.01); *A23L 2/52* (2013.01); *A23L 33/16* (2016.08); *A61K 33/00* (2013.01); *A61K 33/06* (2013.01); *A61K 33/08* (2013.01); *A61K 33/24* (2013.01); *A61K 33/26* (2013.01); *A61K 33/30* (2013.01); *A61K 33/34* (2013.01); *A61K 45/06* (2013.01); *B01J 8/02* (2013.01); *C02F 1/705* (2013.01); *C11D 3/0005* (2013.01); *C11D 3/044* (2013.01); *A23V 2002/00* (2013.01); *C02F 2103/026* (2013.01); *C02F 2305/04* (2013.01)

(58) Field of Classification Search
None
See application file for complete search history.

(56) References Cited

U.S. PATENT DOCUMENTS

2014/0178491 A1* 6/2014 Back ................ C02F 1/281
424/600

FOREIGN PATENT DOCUMENTS

KR    1020090075718    *  6/2010

* cited by examiner

*Primary Examiner* — Jennifer A Berrios
(74) *Attorney, Agent, or Firm* — Whitham, Curtis & Cook, P.C.

(57) ABSTRACT

Methods and systems are provided for producing ionized alkaline solutions (e.g. ionized alkaline water) that exhibit long-term stability when stored at room temperature.

4 Claims, 4 Drawing Sheets

PRODUCTION OF HIGHLY IONIZED ALKALINE WATER USING A COMBINATION OF REDUCING METALS AND REDUCTIVE MINERALS

BACKGROUND OF THE INVENTION

Field of the Invention

The invention generally relates to improved methods and systems for producing ionized alkaline solutions that are stable. In particular, the invention provides methods and systems that employ a medium comprising reducing metals and reductive minerals to produce very stable ionized alkaline solutions such as ionized alkaline water.

Background of the Invention

The consumption of ionized alkaline water is purported to achieve a variety of health benefits, including slowing ageing and preventing disease, and water ionizers (also known as alkaline ionizers) have become popular home and commercial devices. Ionized alkaline solutions are also used as cleaning and disinfecting agents. Most devices utilize Electrolyzed Oxidizing (EO) water technology to raise the pH of water (or another ionic liquid such as brine) via ionization via contact with an electrochemical cell. Generally, an electrical current is passed through the electrochemical cell creating an electrolysis reaction which "splits" or disassociates water molecules by removing or adding electrons, creating positively charged hydrogen ions (H+) and negatively charged hydroxyl ions (OH−). The electrochemical cell incorporates two electrodes and an ion exchange membrane that allows each electrode to attract ions that have an opposite charge. For example, positively charged ions (cations, e.g. H+) move towards the electron-providing (negative) cathode and negatively charged ions (anions, e.g. OH−) move towards the electron-extracting (positive) anode. EO water technology captures the resultant acidic and alkaline solutions at the cathode and anode, respectively.

Characteristic properties of EO solutions include pH and oxidation-reduction potential (ORP). The pH of the acidic solution typically ranges from about 2.1 to 5.5 and the ORP ranges from about +650 millivolts to +1100 millivolts. The pH of the alkaline solution generally ranges from about 8.5 to 12.0 and the ORP ranges from about −250 millivolts to −700 millivolts. Typical applications of the two EO water solutions are: the acidic solution with its highly positive ORP is an excellent sanitizer/disinfectant, especially when made using a brine ionic solution; and the alkaline solution with its very negative ORP has excellent surfactant and emulsifying properties and is thus often used for or in cleaning formulations.

Unfortunately, both the acidic and alkaline solutions captured in the EO water process are highly unstable due to the high level of ionization, the high positivity of the ORP of the acidic solution and the high negativity of the alkaline solution. Both solutions are very reactive and decompose rapidly in heat, light and air. Thus, one of the biggest limitations of EO water technology is that the shelf-life of both acidic and alkaline water solutions is very short.

SUMMARY OF THE INVENTION

The present disclosure provides an alternative technology for producing ionized alkaline water, referred to herein as "ion dispersion" (ID). ID also uses an electrolysis reaction to create ionized water. However, instead of an electrical current, ID technology utilizes reducing metals and reductive minerals to ionize water molecules. For ID, a selected combination of metals and minerals is used to produce a reducing composition and an ionic liquid such as water or other aqueous liquid is ionized upon contact with the composition, e.g. when filtered through the composition. Unlike an EO electrochemical cell that operates with fixed parameters (e.g. a fixed electrical current, usually 32 amps and 16 volts; water flow of 1 liter per minute; and a contact time of 16 milliliters per second), with ion dispersion, the composition of the minerals and metals, the flow rate and the contact time can be varied or "tuned" to obtain varying degrees of ionization and other alkaline water properties. For example, the slower the flow rate and longer the contact time between the ionic solution and the ionizing media, the greater the degree of ionization. Therefore, the degree of ionization can be altered by changing these parameters. ID technology is thus used to produce ionized products (e.g. ionized alkaline water) with desired characteristics (e.g. high stability).

Accordingly, embodiments of the invention provide blends or mixtures of several different reducing metals and minerals which, when exposed to an ionic (ionizable) liquid such as water, cause a slow, time-release reaction to occur that "splits" components of the ionic liquid (e.g. water) into ions. In one aspect, the ionic liquid is or includes water, and contact of the water with a metal and mineral mixture of the invention results in production of H+ (hydrogen) and OH− (hydroxyl) ions. Significantly, and in contrast to the prior art, in one aspect, the metals and minerals are selected so that the reaction proceeds slowly, resulting in a stable product that retains its alkaline and ionized properties over a long period of time, and thus advantageously has a long shelf-life (a day or more to 10 days or more to 200 days or more, etc.). While there are a number of metals that vigorously split water (e.g. lithium and calcium) the end result is relatively unstable alkaline water having very short lived properties and shelf-life much like EO alkaline water. Thus, these metals are generally not preferred or optimal for use in the claimed compositions, but may be used in particular compositions and excluded from others. In general, the compositions comprise metals from the less reactive Group II metals, together with rare earth minerals, various metal reducing agents and mineral buffers, as described in detail below.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

In one aspect, what is provided herein is a medium for ionizing an ionizable liquid. The medium comprises: about 50% by volume of one or more group II elements; about 15% by volume of one or more rare earth minerals; about 30% by volume of metal reducing agents; and about 5% by volume of a mineral buffer.

In another aspect, what is provided herein is a method of producing an ionized alkaline liquid, comprising a step of contacting an ionic liquid with a medium comprising: about 50% by volume of one or more group II elements; about 15% by volume of one or more rare earth minerals; about 30% by volume of metal reducing agents; and about 5% by volume of a mineral buffer; wherein the step of contacting is carried out for a period of time sufficient to ionize ionizable molecules in said ionic liquid. The step of contacting may be carried out by flowing the ionic liquid through the medium, or by static exposure of the ionic liquid to the medium.

Other aspects of this disclosure provide stable ionized alkaline water with an oxidation-reduction potential (ORP) of −250 or lower (e.g. at most about −250), wherein said stable ionized alkaline water is stable for at least one day. In some aspects, the pH of the stable ionized alkaline water is from about 8.5 to about 10.0. In some aspects, the stable ionized alkaline water retains its pH and ORP for at least 240 days when stored at room temperature.

Also provided herein are devices for producing ionized alkaline solutions. The devices comprise a compartment for containing a bed of medium comprising about 50% by weight of one or more group II elements; about 15% by weight of one or more rare earth minerals; about 30% by weight of metal reducing agents; and about 5% by weight of a mineral buffer. The compartment is configured so as to permit an ionic liquid to make contact with the medium.

In some aspects, the compartment is configured to receive a cartridge housing the medium. In other aspects, the compartment is configured to receive the medium directly within the compartment. In some aspects, the compartment is configured so that the ionic liquid flows through the bed of medium. In other aspects, the compartment is configured so that a surface of the ionic liquid contacts a surface of the bed of medium. In some aspects, the device is a pet watering bowl or fountain.

Also provided are potable or comestible products comprising or made with stable ionized alkaline water, wherein the stable ionized alkaline water has an oxidation-reduction potential (ORP) of about −250 or lower, and wherein the stable ionized alkaline water is stable for at least one day. The potable or comestible product may be, for example, coffee, purified drinking water, an enhanced sports performance drink or a soft drink such as a carbonated cola.

Also provided are therapeutic compositions comprising i) stable ionized alkaline water, wherein the stable ionized alkaline water having an oxidation-reduction potential (ORP) of about −250 or lower, wherein the stable ionized alkaline water is stable for at least one day; and ii) at least one therapeutically active agent.

Also provided are cleaning solutions comprising stable ionized alkaline water, wherein the stable ionized alkaline water has an oxidation-reduction potential (ORP) of about −250 or lower, and the stable ionized alkaline water is stable for at least one day; and at least one additional agent such as one or more surfactants, chelating agents, and sodium hydroxide.

DETAILED DESCRIPTION

Figure 1A:
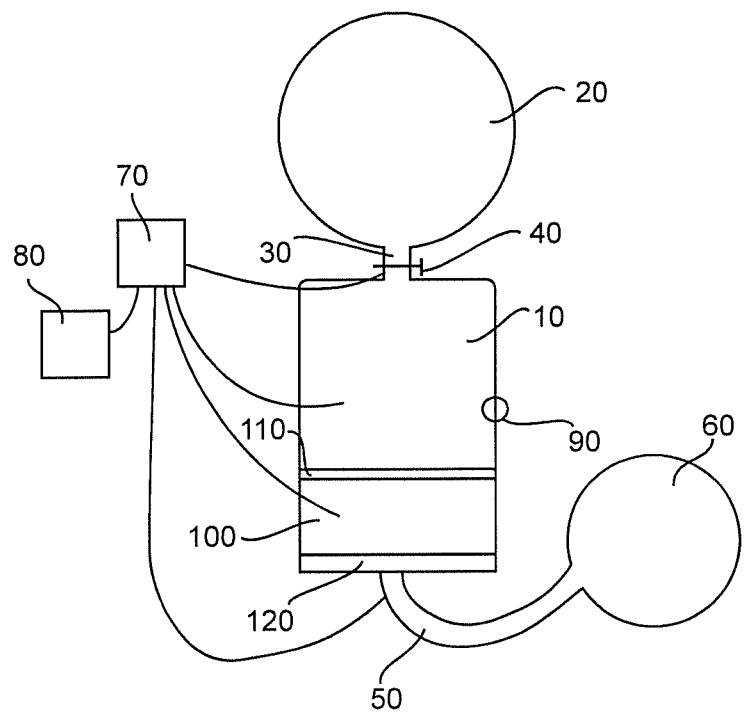
FIGS. 1A and B. Schematic illustrations of exemplary water filtration systems that utilize the compositions described herein. A, down-flow system; B, up-flow system.

Compositions provided herein are used as media (e.g. filtering media) to advantageously produce stable, ionized alkaline liquids (e.g. ionized alkaline water). Upon contact with the media, ionic liquids (e.g. water) ionize into component ions (e.g. OH− and H+), which are released into the surrounding milieu. The components of the media and the conditions of contact between the ionic liquid and the media are selected so that the ionization reaction proceeds at a desired or predetermined rate to produce an ionized alkaline solution with desired properties such as a particular pH, ORP, hypertonicity and osmolarity, or particular ranges thereof. For example, a long contact time results in production of a highly alkaline hypertonic solution that is excellent for cleaning, degreasing and emulsifying, while a shorter contact time produces a solution with less alkalinity but with excellent hydration properties. In contrast to EO water technology, in the present ID devices, there is no requirement for a membrane to separate the positive and negative ions, so partitioning and/or collection of the alkaline and acidic solutions is advantageously not required. Instead, the positive ions (H+) generated during exposure to the medium react to form a small amount of hydrogen gas that is released from the solution either actively (e.g. by evacuation from a filter device via a pressure relief valve) or passively (e.g. into the atmosphere) in the case of static devices. The remaining solution is an OH— (hydroxyl) rich alkaline solution.

The following definitions are used throughout:

pH is a measure of the acidity or basicity of an aqueous solution. Solutions with a pH less than 7 are said to be acidic and solutions with a pH greater than 7 are basic or alkaline. Pure water has a pH very close to 7.

pKa is the negative base −10 logarithm of the acid dissociation constant of a solution: pKa=−log 10 Ka. The lower the pKa value, the stronger the acid.

Electrolysis—The passage of a direct electric current through an ionic substance such as brine or mineral water resulting in chemical reactions at the electrodes and separation of individual components of the ionic substance. For example, brine solution is split into ions of Na+ (sodium) and Cl− (chloride) and water is split into ions of H+ (hydrogen) and OH− (hydroxyl).

Ionization—Ionization is the process by which an atom or a molecule acquires a negative or positive charge by gaining or losing electrons to form ions, often in conjunction with other chemical changes.

Oxidation-reduction potential—In aqueous solutions, the oxidation-reduction potential is a measure of the tendency of the solution to either gain or lose electrons when it is subject to change by introduction of a new chemical species or physical forces such as electrical energy, high pressure or extreme heat or cold Reducing agent—A reducing agent, or reductant, loses electrons in a chemical reaction. A reducing agent typically is in one of its lower possible oxidation states and is known as the electron donor. Examples of reducing agents include the earth metals, formic acid, and sulfite compounds.

Hypertonic—A hypertonic solution is one with a higher concentration of solutes when compared to another solution from which it is separated by a semipermeable membrane.

Hypertonic thus refers to a greater concentration. Solute molecules that can do so (those for which the membrane is permeable) tend to move across the membrane from the area of higher concentration to the area of lower concentration. For example, in biology, a hypertonic solution is one with a higher concentration of solutes outside the (semipermeable membrane of) the cell than inside the cell. When a cell is immersed in a hypertonic solution, the tendency is for water to flow out of the cell, thereby dehydrating the cell. Ionized alkaline solutions are considered "hypertonic" when the pH is greater than about 10.5 and the ORP is less than about −600 mvolts. Hypertonic solutions are especially useful for cleaning, degreasing and emulsifying and can be the base solution for or a component of cleaning fluids, disinfectants, sanitizers, etc.

Osmolarity—This is the measure of solute concentration, defined as the number of osmoles of solute per liter of solution.

A "rare earth element" (REE) or "rare earth metal" as defined by IUPAC is one of a set of seventeen chemical elements in the periodic table, specifically the fifteen lanthanides, as well as scandium and yttrium.

A "rare earth mineral" is a mineral which contains one or more rare earth elements as major metal constituents.

As used herein, "metal reducing agents" refers a metal that loses electrons in a chemical reaction.

As used herein, "mineral buffers" refers to mineral and alloys which serve to buffer a liquid within a desired pH range.

Adiabatic: An adiabatic process is one that occurs without transfer of heat or matter between a system and its surroundings. Adiabatic ionization refers to a form of ionization in which an electron is removed or added to a molecule in its lowest energy state forming an ion in its lowest energy state.

Brine is a solution of salt (usually sodium chloride, but other salts may also be used) in water. In different contexts, brine may refer to salt solutions ranging from about 3.5% (a typical concentration of seawater, or the lower end of solutions used for brining foods) up to about 26% (a typical saturated solution, depending on temperature).

Potable: a potable liquid is safe/suitable for drinking.

Semi-permeable: permeable to liquids such as water, but not to the media described herein.

Blends and Combinations

The present disclosure provides media comprising blends of multiple reducing metals and minerals which, when in contact with an ionic solution, cause a slow, time released reaction that splits components of the ionic solution, particularly water, into H+ (hydrogen) and OH− (hydroxyl) ions. The slow, time release reaction results in production of very stable end products such as Ion Dispersion (ID) alkaline water. In some aspects, Ion Dispersion (ID) technology utilizes reactive metals from the Group II Period Table of Elements, combined with other metals and minerals that attenuate or moderate the reactions.

Group II elements of the periodic table are called alkaline earth metals and include elements such as beryllium, magnesium, calcium, strontium, and barium, although the practice of the invention is not limited to the use of these five, or even to the use of Group II elements (e.g., lithium, although not preferred, can be used in some mixtures).

Compositions provided herein comprise one or more Group II elements combined with one or more rare earth elements. Rare earth elements include but are not limited to: scandium, yttrium and the 15 lanthanide elements (lanthanum, cerium, praseodymium, neodymium, promethium, samarium, europium, gadolinium, terbium, dysprosium, holmium, erbium, thulium, ytterbium, and lutetium). As used herein, rare earth elements are generally in the form of mineral ores. Exemplary rare earth minerals and mineral ores which often contain significant rare earth substitutions include but are not limited to: aeschynite, allanite, apatite, bastnäsite, britholite, brockite, cerite, fluocerite, fluorite, gadolinite, monazite, parasite, stillwellite, synchysite, titanite, wakefieldite, xenotime and zircon.

The third group of media components includes one or more metal reducing agents. This group of components includes but is not limited to: manganese, iron, zinc, copper and silicon. These components are used to balance or attenuate the relatively vigorous reaction of the Group II elements, and thus their inclusion results in a slowing of the ionization reaction between the medium and the ionic liquid that is ionized, compared to the rate at which the reactions would occur if these metal reducing agents were not included.

The fourth media component is one or more mineral buffers (e.g. a mixture of two or more mineral buffers may be combined). Mineral buffers also slow down the reaction between the medium and the ionizable liquid, and tend to stabilize ionized liquid. The final selected volume of buffers in a blend varies depending on the system design. Exemplary mineral buffers include but are not limited to: tourmaline, calcium carbonate, aluminum oxide, quartz silica, borosilicate, etc.

Accordingly, compositions described herein comprise a mixture of Group II elements, rare earth minerals, metal reducing agents, and mineral buffers, each of which is defined/described above. Tailoring the components and percentages of each type of metal and mineral that is included in a media mixture, a media suitable for making ionized alkaline solutions with long-term stability and other desirable properties is produced. Generally, Group H elements represent from about 30 to 70% of the mixture but depending on the element can comprise up to about 85% (e.g. they are present in a range of from about 30, 35, 40, 45, 50, 55, 60, 65, or 70% by volume, and may be present at about 75, 80 or 85%); the rare earth minerals are present as about 10 to 20% (e.g. from about 10, 11, 12, 23, 14, 15, 16, 17, 18, 19 or 20% by volume); metal reducing agents are present as about 1 to 50% of the mixture (e.g. from about 1, 2, 3, 4, 5, 10, 15, 20, 25, 30, 35, 40, 45 or 50% by volume), and the mineral buffers are present in a range of from about 1 to 25% of the mixture (e.g. in a range of from about 1, 2, 3, 4, 5, 6, 7, 8, 9, 10, 15, 20 or 25% by volume).

Tables 1-4 list exemplary elements and minerals that are used to produce ionized alkaline water. It is noted that other elements such as the alkali elements of the Periodic Table produce a very negative oxidation-reduction potential (ORP) and alkaline pH when mixed with water. However, these alkali elements are either too water soluble, too reactive or too toxic to be considered for use in the Ion Dispersion process.

Each element and mineral listed in Tables 1-4 has an associated minimum and maximum percentage. The minimum percentage represents the least amount of the element that can be used to create an electrolysis reaction and the maximum percentage represents the most that can be used to obtain a formulation of stable alkaline water with at least 240 days of shelf-life.

TABLE 1

GROUP II ELEMENTS

| Element | Minimum | Maximum |
|---|---|---|
| Beryllium | Not Used - Toxic | |
| Magnesium | 30% | 70% |
| Calcium | Not Used - Too Soluble | |
| Strontium (Strontianite) | 50% | 85% |
| Barium (Barite - Barium Sulfate) | 60% | 85% |
| Radium | Not Used -Toxic Radioactive | |

TABLE 2

RARE EARTH ELEMENTS

| Element | Minimum | Maximum |
|---|---|---|
| Scandium (Scandium Oxide or thortveitite ore) | 15% | 30% |
| Yttrium (Yttrium-Copper Ore) | 15% | 30% |
| Lanthanum | 10% | 20% |
| Cerium | Not Used due to Fire Hazard | |
| Praseodymium (Monazite or Bastnäsite ore) | 10% | 20% |
| Neodymium | 15% | 30% |
| Promethium | Not Used due to being Radioactive | |
| Samarium | Not Used -not electronegative | |
| Europium | Not Used - too water soluble | |
| Gadolinium | Not Used -toxic | |
| Terbium (Monazite) | 10% | 20% |
| Dysprosium (Monazite and Bastnäsite ores) | 10% | 20% |
| Holmium (Monazite and Bastnäsite ores) | 10% | 20% |
| Erbium (Monazite and Bastnäsite ores) | 10% | 20% |
| Thulium | Not Available | |
| Ytterbium | 15% | 30% |
| Lutetium | Not Available | |

TABLE 3

METAL REDUCING AGENTS

| Metal/Metal Alloy | Minimum | Maximum |
|---|---|---|
| Calcium Calcium Magnesium Alloy | 10% | 45% |
| Aluminum (Calcium Aluminum, Calcium Silicon) | 10% | 30% |
| Iron (Ferrosilicon) | 25% | 50% |
| Tin | Not Used - Too Soluble | |
| Copper | 10% | 30% |
| Silver Used to add disinfecting properties to ID Alkaline Water | 1% | 3% |
| Manganese | Not Used - Too Soluble | |
| Zinc | 10% | 30% |

TABLE 4

MINERAL AND ALLOY BUFFERS

| Buffer Compound | Minimum | Maximum |
|---|---|---|
| Calcium Carbonate | 5% | 10% |
| Aluminum Oxide | 5% | 10% |
| Tourmaline | 5% | 25% |
| Silica (Quartz) | 5% | 10% |
| Borosilicate | 5% | 10% |

An exemplary generic ratio of the components is as follows:

| | |
|---|---|
| Group II elements | 50% |
| rare earth minerals (ores) | 15% |
| metal reducing agents | 30% |
| mineral buffer | 5% |

Exemplary formulas for media to make ionized alkaline water are provided below:

I.

| | |
|---|---|
| Magnesium | 50% |
| Yttrium-Copper | 30% |
| Calcium Magnesium Alloy | 15% |
| Silica | 5% |

II.

| | |
|---|---|
| Strontium | 45% |
| Monazite | 10% |
| Zinc | 10% |
| Copper | 10% |
| Tourmaline | 25% |

III.

| | |
|---|---|
| Strontium | 65% |
| Monazite Ore | 15% |
| Calcium Magnesium | 15% |
| Calcium Carbonate | 5% |

IV.

| | |
|---|---|
| Barite | 65% |
| Calcium Magnesium | 30% |
| Calcium Carbonate | 5% |

V.

| | |
|---|---|
| Magnesium | 30% |
| Strontium | 20% |
| FerroSilicon | 25% |
| Monazite | 20% |
| Calcium Carbonate | 5% |

VI.

| | |
|---|---|
| Magnesium | 40% |
| Monazite | 20% |
| Yttrium-Copper | 20% |
| Calcium Aluminum | 10% |
| Quartz | 5% |
| Aluminum Oxide | 5% |

VII.

| | |
|---|---|
| Magnesium | 30% |
| Neodymium | 30% |
| Zinc | 10% |
| Copper | 25% |
| Calcium Carbonate | 5% |

VIII.

| | |
|---|---|
| Magnesium | 60% |
| Calcium Magnesium | 10% |
| Tourmaline | 30% |

-continued

| IX. | |
|---|---|
| Strontium | 40% |
| Bastnäsite Ore | 20% |
| Ferrosilicon | 15% |
| Silver | 2% |
| Tourmaline | 23% |

| X. | |
|---|---|
| Magnesium | 65% |
| Monazite | 15% |
| Zinc | 5% |
| Copper | 10% |
| Borosilicate | 5% |

All components of the mixtures are readily available, and can be sourced, for example, through water treatment companies, metal treatment and/or etching companies, mining companies, etc. The components are generally provided and incorporated into the mixtures described herein as solid, dry granular particulate products. Some components (e.g. magnesium, zinc and copper) may be in the form of pure metals. Alternatively, various alloys may be employed. Some components are provided and used as ores, e.g. perryite, gadolinite, monazite, bastnosite, etc. Mineral buffers are generally granular products. The resulting media compositions are thus generally also granular in nature. The particles in the media are large enough to allow an ionic liquid to pass between them, but fine enough to cause the liquid to traverse a bed of medium slowly, e.g. at a desired speed which allows the ionizing and alkalinizing reactions described herein to proceed at a suitable, desired rate. Exemplary mesh sizes of the particulate components are about 8×30, 12×30, 12×40 and/or 20×40, and vary with the particular system or device in which the medium is used, and/or with the goals of media use, e.g. whether very slow or moderately slow transit times of an ionizable liquid through the media are desired.

Methods of Using the Compositions

This disclosure provides methods of using the compositions described herein as media to ionize and alkalinize ionic solutions. The methods generally involve exposing an ionic liquid to (contacting an ionic liquid with) the media for a period of time and under conditions sufficient to permit ionization of the liquid by interactions with the media.

In some aspects, the methods are carried out by forming the medium into a permeable bed and flowing the ionic liquid through the permeable bed. In other words, the medium is used as a filter and the ionic liquid passes through the interstices of the particles of the composition in the filter and then leaves or drains out of the medium, generally into a receptacle or conduit leading to a receptacle. The filter may be in the form of a cartridge. In various aspects, the flow of liquid is driven by gravity feed and/or by external pressure, e.g. by a pumping mechanism. The ionic solution is generally treated in a single passage through the filtering medium, but multiple passages through the medium may also occur (e.g. by circulating treated solution) back to and through the medium). Alternatively, the ionic solution may be filtered though or exposed to multiple (a plurality) of media filters in a series. Each filter in the series may be the same or different, and treated solution may be removed from the system at any point between filters, so that treated solutions with different properties may be produced at different points in the system. In some aspects, an ionic liquid is treated by flowing through a filter or filters and is then stored and maintained in a container comprising media (i.e. is stored in static contact with media, as described below), to better preserve the qualities of the treated liquid.

Other methods include contacting the medium with the ionic liquid in a "static" manner, i.e. the two are placed in contact with each other via surface or interfacial contact e.g. through a semi-permeable barrier such as a screen or mesh, rather than by passage of the medium through a bed of medium. In static methods, the molecules that react are principally at the liquid-medium interface (understanding that the liquid may penetrate the medium to an extent). However, over time due to e.g. diffusion of ions away from the interface and into and within the liquid, (e.g. to areas of lesser concentration) the entire body of liquid will gradually take on and maintain the characteristics of liquid that is exposed directly to the medium (will be ionized and alkalinized). In such aspects, liquid may be circulated past (but not through) the medium, e.g. with a pumping mechanism, or by another mechanism that agitates the liquid (e.g. shaking, mixing, etc.), either mechanically or manually.

In yet other aspects, the methods are carried out by dispersing or placing the medium within or in an ionic liquid for a period of time sufficient to allow reactions between the medium and the liquid to occur. Then, the medium is removed from the liquid which has been ionized and alkalinized during the contact. For example, the particulate compositions may be added directly to an ionic solution and then mixed or agitated to disperse the medium throughout the liquid, and then, after a suitable period of time, the medium is allowed to settle and the liquid is decanted, or the media particles are removed from the solution by filtration, centrifugation, etc.

In yet other aspects, the methods are carried out by suspending medium in an ionic liquid via a pouch or "tea-bag" which is formed from a semi-permeable material and which contains the medium, and allowing contact between the medium in the tea bag and the surrounding liquid to take place across or through holes/pores, etc. in the semi-permeable material. The teabag may be retained indefinitely in the ionized alkalinized liquid that is produced, or may be removed from the ionized alkalinized liquid when a desired level of ionization has been attained.

In yet other aspects, the methods are carried out by attaching the medium to a solid support, e.g. by being capturing or trapping it within a permeable casing, or solidifying and/or attaching it via an adhesive, e.g. as a "lollipop". The support may be in the form of a wand or stick, e.g. for immersion in and/or stirring of individual portions of an ionic liquid such as water, to produce personal, individualized servings of ionized alkaline water.

In all methods, the devices, compartments, etc. comprising medium may be designed for multiple uses, or may be single use (disposable) products.

Ionic liquids that can be treated (ionized and alkalinized) in this manner include but are not limited to: water (which can be activated charcoal filtered water, tap water, bottled water, spring water, etc.); brine (see definition above); liquids which contain one or more agents of interest (e.g. a drug, a medicament, a natural product, a flavoring or colorant, vitamin, health-care related agents, cleaning agents, surfactants, oils, etc.). In such aspects, the liquid that is treated contains the one or more agents prior to and during treatment, and the one or more agents may or may not be ionizable.

Reactions between the Compositions and Ionic Liquids

The reactions that take place between ionic solutions that are exposed to the compositions (media) described herein are based on the following: ionization energy (IE) refers to the energy required to remove a single electron from a single atom or molecule. In chemistry, the ionization energy is typically specified as a molar quantity (molar ionization energy or enthalpy) i.e. the amount of energy it takes for all the atoms in a mole to lose one electron each) and is reported in units of kJ/mol or kcal/mol. Ionization energy is related to the number of electrons in the outer shell of an atom and to the size of the atom or molecule. Larger molecules tend to have lower ionization energies because the outer shells of their atoms shield the nucleus from the outer electrons, thereby decreasing the attraction of the nucleus for the outer electrons and decreasing the amount of energy required to remove them. In addition, molecules with fewer electrons in the outermost ("valence") shell tend to exhibit lower IEs; removal of electrons from the outermost shell leaves the next shell with a full complement of electrons, a stabilizing factor which counterbalances the otherwise energetically unfavorable effects of incurring a negative charge. A goal when selecting the components and ratios of components in the blends and combinations of the invention is to create a medium with a low IE, yet which can still ionize the water molecules of the solution to a sufficient extent.

Alkali metals have only one electron in their valence shell. These atoms have a strong desire to lose that electron (IE is low) so they can attain a more energetically stable noble gas configuration with a complete outer shell, which is overall relatively energetically favorable, in spite of the development of a positive charge. Thus, alkali metals such as potassium, sodium, rubidium, etc. have low ionization energies (e.g. 419 kJ/mol for potassium) and readily ionize. However, the alkali metals are too reactive and too water soluble for use in filtering devices. Therefore, the largest percentage of metals in the ID combinations of the invention is that of the Group II alkaline metals, which have two electrons in the outer valence shell. These metals are ionizable but the IEs of ionization are higher than those of the alkali metals, and they are thus less reactive, more stable and well-suited for use in filtering media.

Substances that have the ability to reduce other substances (cause other substances to gain electrons) are referred to as reductive or reducing agents (reductants, reducers, electron donors, etc). Reducing agents transfer or donate electrons to other substances and in so doing are oxidized. Conversely, substances that have the ability to gain or accept electrons are referred to as oxidizing agents or electron donors and are themselves reduced in the process. Electron donors can form charge transfer complexes with electron acceptors, and this is the role of the rare earth mineral ores and electropositive metal reducing agents in the ID metal and mineral mixtures described herein. These components carry out the transfer of electrons to an ionic solution such as water, resulting in ionization of water molecules.

Properties of the Ionized Alkaline Solutions and how to Achieve Desired Properties The properties of the ionized alkaline solutions that are produced by the methods and systems described herein vary based on several parameters, including the composition of the medium, the extent and time of contact between the ionic liquid and the medium, flow rates, the type of ionic liquid that is treated, etc.

In general however, the pH of the ionized alkaline solutions produced by the methods and systems described herein are in the range of from about 10.5 to about 12.0, e.g. about 10, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, or 12.5.

The oxidation-reduction potential (ORP) of the solutions is generally at least about −250 or lower, and may be e.g. in the range of from about −250 millivolts to about −700 millivolts, e.g. about −250, −275, −300, −325, −350, −375, −400, −425, −450, −475, −500, −525, −550, −575, −600, −625, −650, −675, −700, −725 or −750 millivolts.

The amount of energy required to split or disassociate electrons from the ionic solution via chemical reduction using the compositions described herein is very small, and the resulting solutions are in a relatively low energy state. Low energy state ID alkaline solutions are less reactive than EO water alkaline solutions or alkaline solutions produced from electrolysis. As a result, the ionized alkaline solutions prepared as described herein are stable in heat, cold, light and air. For example, the usual shelf-life of such a solution is generally at least about one day, about one week, about one month, and may be much longer, e.g. up to one year or more, and can range from at least about 240 days to about 365 days or longer, e.g. up to 2 years or more, when stored e.g. at room temperature.

One characteristic of the alkaline solutions described herein is hyper-tonicity. Both EO alkaline solutions and ID alkaline solutions exhibit natural surfactancy. However, that of ID alkaline solutions is stronger due to their hyper-tonicity. A hypertonic solution attracts moisture and thus has a dehydrating effect. The product is thus excellent for cleaning, emulsifying, degreasing, etc. and these properties can be enhanced, e.g. by the addition of other compatible chemicals, essential oils, plant extracts, etc. to make a strong disinfectant.

A goal of manufacturing a hypertonic solution is to create a solution with properties similar to those of a 2% sodium hydroxide solution. 2% NaOH solutions were used for cleaning and disinfecting e.g. in the 1930s to 40s, but are disadvantageous for use with metals due to corrosion. The present solutions advantageously possess equal or similar cleaning properties, without the corrosive side effects.

In contrast, when water flows through an ID filter-type device at a faster rate, the properties are different and the treated solutions tend to be extremely hydrating. This is due to the solution's osmolarity which is less than about 300 milliosmoles. Osmolarity is the measurement of a solution's ability to penetrate across the cell membrane. Measurements less than 300 milliosmoles indicate excellent hydration properties. Hydration energy is the energy released upon contact with the cell membrane. When the highly ionized OH− (hydroxyl ion) contacts the transport proteins embedded into the cell membrane, it creates heat that enables more of the solution to cross the membrane. This is called Active Transport. Thus, ionized solutions with osmolarity in the range of 300 milliosmoles are suitable for consumption, e.g. for drinking or cooking.

Osmolarity and hyper-tonicity are almost opposite concepts. Osmolarity takes into account the total concentration of penetrating solutes, whereas hyper-tonicity takes into account the total concentration of extracting solutes. This means that ID alkaline solutions produced using a fast flow and short contact time have a high concentration of penetrating ions (hydroxyls) while ID alkaline solution produced using slow flow rates and long contact time will not and do not penetrate but rather extract moisture e.g. from cells with which the solution comes in contact, dehydrating them.

The properties of the ionized alkaline solutions produced by the present methods are varied by varying the reaction conditions, including varying the precise composition of the medium and the contact time between an ionic liquid and the medium. The contact time may be influenced e.g. by flow rate and by the volume or depth of medium which is available to interact with the ionic liquid. For example, in a flow-through system, the flow rate and contact time between the ionic solution and the metal/mineral affect the properties of the ionized alkaline liquid that is produced. For example, for water treated using a filter-type device, a greater percentage of water is split into ions of H+ (hydrogen) and OH− (hydroxyl) if the flow rate is relatively slow and/or the volume of medium to which the water is exposed is large. A formula for calculating "empty bed contact time" or "EBCT" is provided below. An EBCT calculation measures that amount of contact, in minutes, that the water or ionic solution is in contact with the ID media. If the EBCT is less than about 4 minutes, then the resulting solution will have a very low pKa, resulting in properties that are hydrating. If the EBCT is longer than about 4 minutes, then the solution will have a higher pKa and becomes hypertonic. To achieve the maximum pKa of e.g. 13.8, the contact time must generally be greater than about 6 minutes.

For a static system, the properties vary according to e.g. the surface area of medium to which the ionic liquid is exposed, the length of time of exposure, For example, a 6-inch round mesh dish that is about 3 inches in height holds about 1 pound of ID media. Such a disk will ionize 1 gallon of water in about 6 hours, providing a hydrating solution with a low pKa and pH measurements between about 8.5 and 9.5, and an ORP between about −250 mvolts and −400 mvolts. It is noted that a static filtration system is generally not capable of producing hypertonic solutions because of the minimal contact between the ionic liquid and the media.

Systems and Devices

The ionizing and alkalinizing media described herein may be used in a variety of systems and devices, including but not limited to: flow-through filtering systems, including various tank-type systems and various cartridge systems; and static or static exposure systems. In the devices, the metals and minerals that make up the ionizing/alkalinizing medium are positioned in a variety ways. For example, the medium components may be layered into a suitable medium-containing portion of a device, or may be premixed together into a relatively homogeneous mixture and then placed in the medium-containing portion of a device, or one or more components may be blended together while others are placed in the medium containing portion of the device in separate layers, etc. All such styles of using the media are encompassed herein.

Flow-Through Filtration

Flow-through filtration refers to an aspect of the invention in which the water (or other ionic fluid) that comes into contact with the ID medium flows or is flushed through the medium at a desired rate, to achieve a desired level of ionization and alkalization. In flow-through filtration, a given quantity of liquid enters a bed of media, passes through and then exits the bed, usually in a single passage, although systems designed to create multiple and/or continuously recirculating passages are also encompassed. Such systems may be large scale, e.g. of a size that allows treatment of the entire water supply of a house, or which can be used in a factory which manufactures ionized alkaline water for sale. Alternatively, such systems may be much smaller, e.g. capillary systems to generate ionized alkaline water in a laboratory or medical setting. Intermediately sized devices, e.g. attachments or parts of a coffee or drink preparation machine, are also encompassed. Exemplary flow/filtration systems are described below.

Tank System

In some aspects, the system is a so-called "tank system". Such systems generally comprise a first receptacle or chamber for receiving the medium, configured to allow the formation of a bed of medium through which an ionic liquid can pass, and a means of introducing an ionic liquid into the chamber. The ionic liquid may be placed in a second receptacle, in which case the first and second receptacles are connected so that the ionic fluid can leave the second receptacle and enter the first receptacle that contains the bed of medium, flow through the bed, and then exit the first receptacle. The direction of flow of the ionic liquid may be upward or downward through the media bed. This type of design allows flexibility in achieving the desired solution properties since the contact time between the ionic solution and the medium can be adjusted e.g. by adjusting the flow rate of the ionic liquid and/or the dimensions and composition of the bed of medium.

In an upflow system, as the ionic solution enters the medium via the bottom of the tank, it flows in an upward direction, filling the interstitial space between the media particles. As the ionic solution contacts the metals and minerals, an oxidation-reduction reaction occurs. The ionic solution is stripped of electrons and the ID medium acquires electrons. If the ionic liquid is water, as it is stripped of electrons, it splits into ions of hydrogen (+H), hydroxyl (−OH) and oxygen (O−). Secondary reactions take place within medium in that the hydrogen ions bond together, forming a small amount of hydrogen gas, and the oxygen ions bond together, forming oxygen gas. To minimize or prevent pressure from building up in the tank, an optional pressure relief valve may be installed e.g. at the top of the tank; or an opening may be provided to allow the gases to escape.

The tank system can also be a downflow design. When a downflow design is utilized, the same reactions take place as in the upflow design. The only difference is that the ionic solution enters the ID medium from the top and percolates down through the tank. In some aspects, the pressure of the flow forces the solution up and out of the tank into a collection tube that is connectedly attached to the tank.

The choice of an upflow or downflow strategy depends in part on the particle size of the ID media. The smaller the particle size, the more pressure drop (back pressure) occurs restricting the flow through the medium in the tank. A large pressure drop will result in "channeling" within the medium so that the ionic solution does not make sufficient contact with the medium, resulting in poor solution properties.

FIGS. 1A and B show schematic representations of such flow-through systems. FIG. 1A depicts a down-flow design in which receptacle 10 is operably connected to ionic liquid source 20 via conduit 30 (e.g. a tube or pipe). Flow of ionic liquid from ionic liquid source 20 to receptacle 10 is controlled by flow control mechanism 40, e.g. a valve or system of valves. Optional control/monitoring system 70 may be included, and comprise e.g. various flow meters, pressure gauges, timers, thermometers, etc. to control and monitor the flow rate, temperature, pressure, etc. into and out of the system. Receptacle 10 contains media bed 100, which is protected by semi-permeable barrier 110 and semi-permeable barrier 120. Semi-permeable barrier 120 may completely cover the bottom of receptacle 10 (as shown) or may cover only the opening to conduit/collection tube 50. Conduit/collection tube 50 receives treated water from receptacle 10 and transports it to a desired destination, e.g. optional reservoir 60, or to another receptacle, e.g. a faucet, tubing, directly into a container for sale, etc. Media bed 100 is depicted as positioned at the bottom of receptacle 10. However, other positions may be used, e.g. part way up the receptacle (e.g. leaving a collection space under media bed 100 at the bottom of receptacle 10) or elsewhere. Optional gas discharge mechanism 90 may be included to release $H_2$ gas generated during water treatment.

Optional automated control/monitoring system 70 may be operationally (electrically) connected to various parts of the system, and may comprise e.g. various flow meters, pressure gauges, timers, thermometers, pH and OPR meters, etc. to monitor and control the flow rate, temperature, pressure, water properties, etc. in the system. Control/monitoring system is generally operably (electrically) connected to and under the control of controller 80, which may comprise a computer, display monitor(s), hard drive, software, etc.; and may output directions or instructions to control/monitoring system 70 and receive input from control/monitoring system 70, and may also receive commands from a human operator.

Figure 1B:
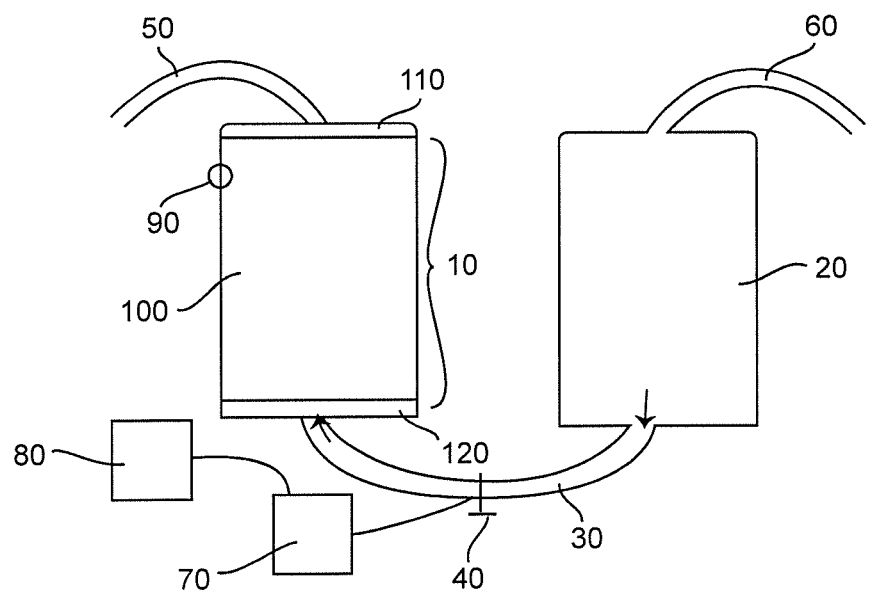

FIG. 1B depicts an alternative up-flow system. In this second system, receptacle 10 houses media bed 100, and semi-permeable barriers 110 and 120 flank and are immediately adjacent to a top portion and a bottom portion of the media bed. As shown, the media bed and barriers occupy most or all of receptacle 10, although this need not be the case. The media bed may occupy less of receptacle 10 than is depicted, e.g. a treated liquid reservoir (not shown) may be present near or at the top of media bed 100, e.g. above semi-permeable barrier 110. Ionic liquid flows from ionic liquid source 20 up into to receptacle 10 via conduit 30, and the flow and flow rate may be controlled by flow control mechanism 40 e.g. a valve or system of valves. Automated control/monitoring system 70, controller 80 and gas discharge mechanism 90 (described above) may also be included in this aspect of the invention and are depicted in FIG. 1B.

The receptacle which contains the media bed may be designed either to receive the medium manually, e.g. by packing the "raw" granular medium into a suitable location in the receptacle. Alternatively, the receptacle may be designed or configured to receive and retain a preformed, prepacked filter or cartridge which contains the medium (described in detail below). If manual filling is desired, the medium may be introduced as layers or as a pre-mixed homogenous composition, or as a combination of these (some components are mixed together but others are layered separately), and semi-permeable barriers may be introduced so as to be positioned on top of and underneath the media bed. Similar principles apply when introducing media into a cartridge or prepackaged filter: the medium may be a homogenous mixture or may be layered, etc.

To achieve desired hypertonic properties, the ionic solution must have a minimum of 4 minutes of contact with the ID medium. An empty bed contact time calculation (EBCT) is used to size the tank and the amount of ID media for a tank system, as follows:

$EBCT = (V \times C)/Q$, where:

V=Volume of ID media (cubic feet)
Q=flow rate in gallons per minute (gpm)
C=conversion factor (7.48 gallons/cubic foot)

For example, to build an ID tank system that flows at a rate of 20 gpm using a 3 cubic foot tank, with a desired EBCT of 1 minute, the amount of media is:

$EBCT = (V \times 7.48)/20$

V (volume of ID media)=2.64 cubic feet.

Flow rates in tank filter designs depend on the design and intended use of the system. For example, a capillary system may have a flow rate in the microliter per minute range, but much larger industrial systems could have flow rates of 500 gallons per minute or more. The weight per cubic foot of any particular ID media will vary depending on the selection of components, and is taken into account when designing systems (e.g. the choice of container material types and strengths, etc.).

Pre-Packed Filters and Cartridges

A prepacked "off the shelf" filter or cartridge design is useful e.g. to attain a fixed flow rate and/or a fixed solution property. Cartridges are generally used for lower flow rates, e.g. up to about 2-3 gallons per minute. The capital cost for a cartridge system is low because common "off the shelf" housings and small amounts of ID media can be utilized. Typical cartridge filter housings are constructed of plastic materials.

Figure 2A:
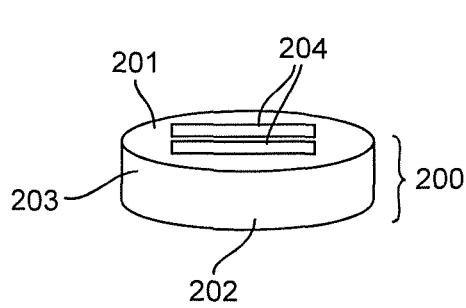
FIG. 2A-E. Schematic illustrations of exemplary pre-packed filters and cartridges described herein. A tilted side view of filter pre-packed with a composition described herein; B, top view of the filter of A, C and D, views of alternative designs for openings in semi-permeable barriers; E, tilted side view of exemplary pre-packed cartridge.
Figure 2B:
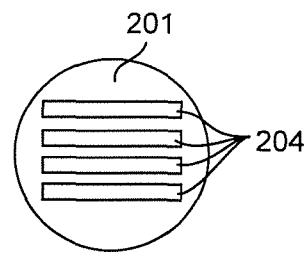
Figure 2C:
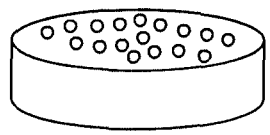
Figure 2D:
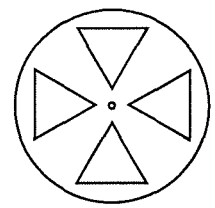

Exemplary prepacked filters are illustrated schematically in FIGS. 2A-D. As shown in side view (tilted) FIG. 2A, filter 200 comprises a top surface 201, a bottom surface 202 (shown in phantom), and an exterior surface 203 (which may be a cylindrical surface if the filter is cylindrical, or a side if the filter is rectangular). Generally, the ionic liquid to be treated flows into filter 200 via openings 204 in top surface 201. A view of top surface 201 with openings 204 (in this case the openings are slots) is shown in FIG. 2B. (It is noted that bottom surface 202 of filter 200 may appear similar or identical when viewed from the bottom.) An alternative style of filter, where the openings are holes or pores, is depicted schematically in FIG. 2C; and a top view of yet another exemplary style of filter (openings are triangular) is shown in FIG. 2D. Those of skill in the art will recognize that many alternative designs are possible in which the shape and size of the filter and openings and other parameters are varied and combined, and all such variants are encompassed herein. Further, in some aspects, an additional semi-permeable barrier (e.g. a fabric, screen, mesh, fibers, etc.) is present between a surface of the media and openings in a surface of the filter, to further insure media retention within the filter.

Figure 2E:
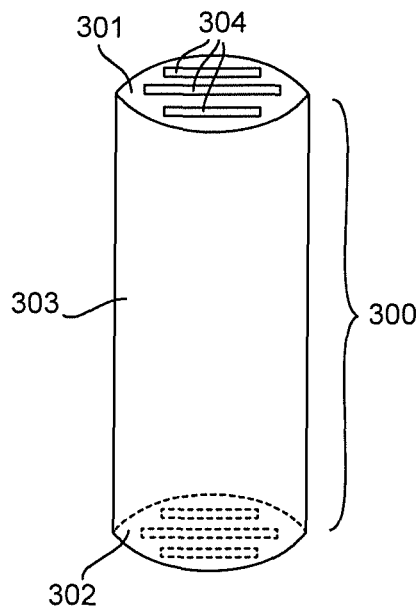

FIG. 2E schematically depicts an exemplary cartridge 300 with top surface 301, bottom surface 302 (shown in phantom), exterior surface 303, and openings 304 (shown as slots). As is the case for the filters described above, although cartridge 300 is depicted as cylindrical, it may be of any suitable shape (e.g. rectangular, etc.) or dimensions, and the patterns of openings may be of any of many suitable shapes, so long as a flow of ionic liquid into the cartridge and a flow of treated ionized alkalinized liquid out of the cartridge is possible.

In some aspects, the ionic solution flows into the bottom of the filter housing and comes into contact with the ID media as it flows up through the cartridge and out the top. The principle of EBCT (empty bed contact time) for cartridge filters is the same as for a tank filter. Cartridge filters are designed to achieve either hydration or hypertonic. For example, to achieve a hypertonic solution with the cartridge filter, the water must have a minimum of 4 minutes of contact time. A typical cartridge housing will hold about 3 pounds of ID media. Therefore the flow rate required is as follows:

$$EBCT = (V \times C)/Q$$

V=Volume of Ion Dispersion Media (cubic feet)
Q=Flow Rate (gpm)
C=Conversion Factor (7.48 gallons/cubic foot)

The Ion Dispersion weight is based on the combination of metals and minerals used. As noted above, there are many combinations of Group II metals, rare earth ores, alkaline or alkali metals and buffers that may be used. When designing a tank filter or cartridge filter, it is important to determine the weight per cubic foot of the ID media and take it into account in the design. For example, if an ID medium with a weight of 40 pounds per cubic foot is used, 3 pounds of the media has a volume of 0.075 cubic feet and the flow rate will be: Flow Rate=0.075×7.48=0.561 gallons per minute (assuming that the EBCT is 1 minute and rounded off to the nearest ½ gallon per minute).

Devices which are or which incorporate such flow-through technology include but are not limited to: large machines for manufacturing (and optionally bottling) ionized alkaline water on an industrial scale; commercial apparatuses designed to process relatively large quantities of ionic liquids, e.g. to produce coffee, tea, juices and other potable liquids; to manufacture cleaning fluids; to manufacture compositions comprising one or more drugs or agents beneficial to health; apparatuses for providing ionized alkalinized water for residential dwellings and businesses; or smaller individual attachments or components of e.g. faucets, shower heads, hoses, toilets (to prevent scale buildup); humidifiers; pitchers (e.g. designed to fit on a kitchen countertop); pet "water fountains" (e.g. similar to those which circulate water through activated charcoal filters); etc. Additional applications of this technology are described below.

Static Ionization/Alkalization Systems

Static ionization/alkalization refers to a process in which the ID media described herein is placed in a container so as to contact water that is substantially static, i.e. the water is not flowing through the media in a continuously replenished stream, but a fixed amount (or an amount within a recommended fixed range) is placed in a container comprising media and left in contact with the ID media, e.g. for a recommended period of time. "Static" systems may rely entirely on passive contact between the ionic liquid and the media, but some movement of the liquid in the container is not included, e.g. by shaking; by stirring (e.g. with a hand-held "wand" comprising media, or via a bladder that turns within the container, or via another hand or mechanical stirring mechanism); or by circulation past the media via a pumping mechanism, etc. However, in a static system, the ionic liquid does not generally make a single passage through a media bed but rather a given amount of liquid in introduced into the system and remains in the system, at least a portion of the liquid maintaining constant contact with ID media until either the liquid or the media is removed from the system. Those of skill in the art will recognize that there may not be a "bright line" between static and flow-through technology in all cases (e.g. an ionic liquid may initially flow through a media bed and thereafter maintain contact with the media bed, etc.), and some devices described herein may utilize either or both, in a variety of configurations.

In static filtration devices, the ID media is generally separated from full contact with the ionic liquid by a screen, mesh, fabric, etc. or other porous or perforated barrier that allows extensive contact between the two at the media-liquid interface through openings or pores in the barrier, while largely retaining the media and the ionic liquid within their respective compartments or locations. As water comes into contact with the media at the interface, the ID media slowly ionizes and alkalizes the water with which it comes into contact generating localized areas of ionized alkaline water. With time (and with optional manual or automated circulation of the liquid within its compartment), ions move from areas of high concentration (near the media) to areas of lower concentration so that the entire volume of liquid (or at least a large portion thereof) becomes ionized and alkalinized. Generally, this static process is used to produce hydration properties but not hypertonic properties because the time required to achieve the latter is relatively long and thus impractical for commercial use.

An exemplary generic container suitable for use in this aspect of the invention is depicted in FIG. 3. In this figure, what is depicted is container 400 e.g. a hand-held water bottle, comprising central compartment 401 for receiving and holding an ionic liquid such as water and media location 402. FIG. 3A shows container 400 with media disposed at the bottom and along the sides of the interior of compartment 401. FIG. 3B shows a similar container but in which media location 402 is located only at the bottom of container 400. Removal of cap 403 allows an ionic liquid and/or media to be placed in container 400. In some aspects, media location 402 is a compartment that is built into container 400, and media may be placed in the container by introducing filling the compartment by hand with granular medium. In this example, pores 402 represent openings in a wall of the compartment that faces the liquid in compartment 401 to allow contact between the media and liquid. Alternatively, media may be present at media location 402 as an insertable disc, cartridge or liner that is pre-filled with media. In this case, pores 404 are present in a wall of the disc or liner that faces the liquid in compartment 401 to allow contact between the media and liquid. Those of skill in the art will recognize that the practice of the invention is not limited to these particular designs. The shape and dimensions of compartments that contain media, or of discs, cartridges and liners that comprises media, may vary greatly, as may the type of materials from which they are fashioned.

Systems or containers encompassed by this aspect of the invention include but are not limited to: pots (e.g. flower pots); bottles e.g. hand held "sports"-type bottles used by athletes, sports fans, hikers, etc. or others who want a portable hand-held source of ionized alkaline water; spray bottles; humidifiers; jars; pitchers (e.g. designed to fit on a kitchen countertop); thermoses; pets water bowls; bird baths (e.g. to minimize or prevent the growth of bacteria and algae); and the like.

Figure 3A:
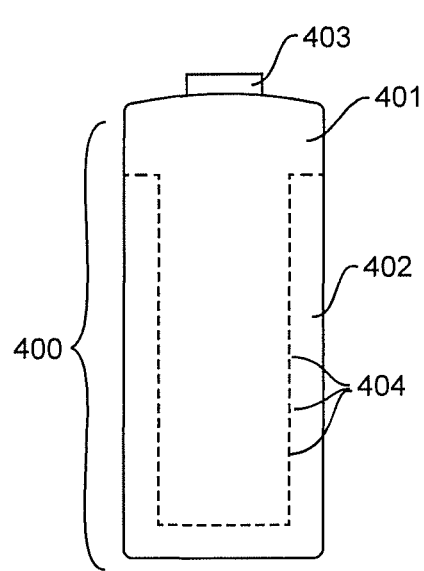
FIG. 3A-D. Schematic illustrations of exemplary devices for making ionized alkalinized liquid, e.g. water. A, exemplary container with media at bottom and sides; B, exemplary container with media at bottom; C, exemplary pet water dish with media at the bottom of the central cavity; D, exemplary pet water dish with media surrounding central cavity.
Figure 3B:
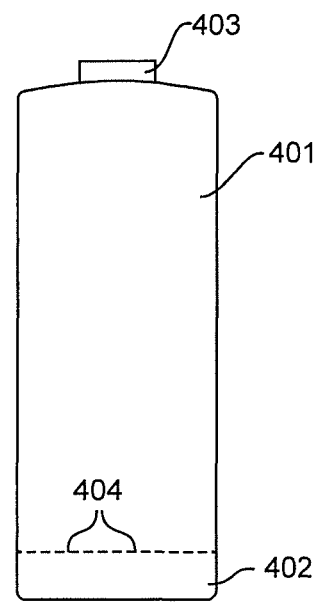
Figure 3C:
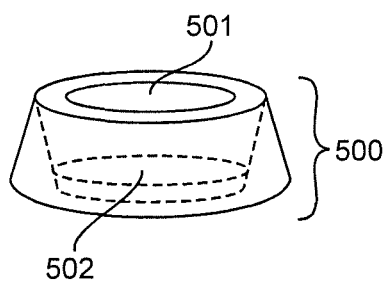
Figure 3D:
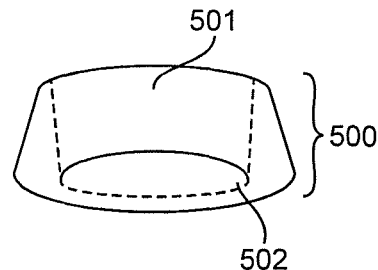

In one aspect, stationary devices include pet water bowls, an example of which is depicted in FIG. 3C. In this figure, watering bowl 500 is shown as comprising central open cavity 501 into which drinking water is placed. In this example, compartment 502 for containing media as described herein is located at the bottom of cavity 501 (shown in phantom). As is the case with other devices which employ static treatment, granular media may be introduced into compartment 502 "by hand", and a screen (e.g. a snap-on disk comprising a screen or other semi-permeable barrier) may be placed over the media; or compartment 502 may be configured to receive a disc or other cartridge that is prepacked with media and which is removably secured in compartment 502, e.g. by sliding, snapping, screwing, etc. the disc into position. FIG. 3D shows a cross-sectional cut-away view of another exemplary water bowl 500 in which compartment 502 extends around most or all of an interior of cavity 501. Compartment 502 may be configured to receive granular media, or to accept e.g. a liner prepacked with media. In all aspects of static treatment, a semi-permeable barrier (permeable to an ionic liquid but not to media) is interposed between the liquid and the media.

Figure 4A:
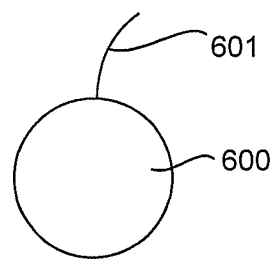
FIG. 4A-B. Schematic illustrations of exemplary devices for making ionized alkalinized liquid, e.g. water. A, "teabag" or pouch; B, media on a support.
Figure 4B:
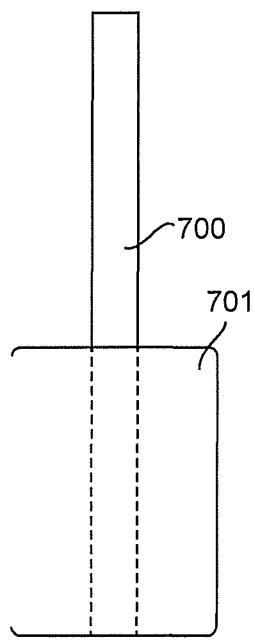

In other aspects, what is provided are what may be termed personalized devices comprising media as described herein for use by individuals. Exemplary aspects include "tea bag" or pouch style media containers that comprise a semi-permeable sac or bag that contains media. A schematic illustration of a "tea-bag" style device is provided in FIG. 4A, where media-containing pouch 600 is shown with optional handle 601, which may be e.g. a solid handle or a flexible string, for controlling the movement of the pouch 600. The pouches may be formed from flexible fabric, mesh, etc., or may be formed from rigid or semi-rigid material (e.g. wire screen, etc.), and may be disposable or reusable. Such pouches may be designed for use, e.g. to treat small amounts of ionic liquid (e.g. to place in a "cup" of liquid to be treated). The "tea bag" is inserted into the liquid and contact is allowed to occur (as described above) for a period of time sufficient to allow a desired degree of ionization and alkalization. Other aspects include devices in the form of a stick or wand of media for "stirring" a glass or container of ionic liquid. A schematic illustration of such a device is provided in FIG. 4B, which shows support 700 with attached media 701. In such devices, ID media is held together and attached a support e.g. by a semi-permeable inert outer coating or by a semi-permeable covering comprising holes or pores (e.g. mesh, wire, cloth, perforated metal or plastic, etc.). Alternatively, a quantity of media may be solidified or agglomerated e.g. by mixing with a suitable binding agent that does not interfere with the media ionizing and alkalinizing properties, and attached to the support in the manner of a "lollipop".

Products

The ionized alkaline solutions provided herein are or are used in a plethora of different products. In some aspects, ionized alkaline water is produced and is sold to customers e.g. as bottled drinking water. In other aspects, the ionized alkaline solutions such as ionized alkaline water are used to manufacture other products. In some aspects, the products are liquids which are made with e.g. ionized alkaline water. In other aspects, the products are liquids which comprise a solvent (which may be water) and one or more solutes of interest, and at least one of the solvent and the one or more solutes is ionizable, and which have been ionized and alkalinized as described herein.

In some aspects, the products are potable liquids or comestible food products that contain or are made with e.g. ionized alkaline water, or which have been treated by the methods described herein. Exemplary liquids include but are not limited to: coffee (including specialty coffees and blends or drinks which include coffee), tea (e.g. conventional teas, herbal teas, chai, blends, drinks which include tea, etc.), juice, milk shakes, smoothies, soups, carbonated soft drinks (e.g. colas and other soft drinks), alcoholic drinks (e.g. wines and liquors), and other potable liquids that are intended for human consumption. Semi-solid comestible products are also encompassed, including but not limited to gelatin containing foods, puddings, sauces, gravies, etc. Other products that may be made with or otherwise include ionized alkaline solutions as described herein include but are not limited to e.g. any food product which includes liquid (e.g. water) as an ingredient, e.g. baked goods, canned goods, pre-packaged dinners in which one or more ingredients have been prepared e.g. in IA water, etc. Such products may also include other ingredients such as NaCl or other salts, coloring, flavorings, acids, buffering agents, etc.

The IA liquids described herein may also be used therapeutically and/or used to formulate therapeutic or health-related products. The products are typically for use in mammals but this is not always the case as other classes of animals (e.g. avian) may also be treated, and the products may be used for plants. In some aspects, the mammal is a human. In some aspects, the animal is a domesticated animal (e.g. a companion pet such as a dog, cat, rabbit, ferret, etc.; a "farm" animal such as a horse, cow, sheep, goat, etc.; or a "wild" animal in a zoo or animal reserve). IA water with high hydrating properties may be used, for example, in various washes, lotions, creams, sprays, rinses, gels, etc. that are administered topically to treat skin disorders, including but not limited to: acne, psoriasis, rashes, eczema, shingles, insect bites, allergic reactions, hives, wounds, burns, scrapes, cuts, incisions, cold sores, cellulitis, impetigo, diaper rash, decubitus ulcers, lichen plantus, dermatitis, blisters, etc. The products generally contain at least one additional active agent (e.g. a drug or medicament, antiseptic agent, etc.); however, IA solutions alone (e.g. IA water) may have beneficial effects for skin disorders.

The IA liquids described herein may also be used as and/or used to formulate personal and/or pet care products. For example, IA water with high hydrating properties may be used in various washes, lotions, creams, sprays, rinses, gels, etc. that are applied topically e.g. cleansing agents and soaps, as hair care products (e.g. shampoos, rinses, etc.), skin care products, tooth pastes, mouth washes, sanitizing wipes or gels, cosmetics, facial "masks", etc. The IA liquids (e.g. IA water) may also be used directly as "soaking" agents, e.g. for feet, hands, etc., or for whole body soaks e.g. in jacuzzis, or may be used as the water in pools for swimming.

The IA liquids described herein may also be used as and/or used to formulate cleaning products. For example, IA water may be used in formulations of descaling products (for water treatment devices, toilets, dishwashers, faucets, humidifiers, etc.); cleaning products such as degreasers, glass cleaners, cleaning solutions for countertops (including metal countertops) and other food preparation surfaces and for cooking surfaces (griddles, burners, etc.); cleaning preparations for leather and synthetic "leathers" (e.g. vinyl, materials formed from plastics, polymers, etc.); for cleaning and disinfecting medical equipment and supplies (e.g. tubing, containers, hospital furnishings (bed frames, tables, chairs, showers, etc.); solutions for cleaning and disinfecting bathroom and/or kitchen fixtures (e.g. surfaces made of porcelain and tile such as toilets, sinks, bathtubs, shower stalls, etc.) as well as faucets, showerheads, etc.; solutions for floor cleaning (e.g. wood floors, tile floors, laminate flooring, etc.); laundry products (e.g. laundry liquid, fabric softeners, rinses, stain removing solution, pre-soak solutions, etc.); solutions for cleaning vehicles, e.g. cars, boats etc. made from e.g. fiberglass, epoxy and polyester resins, etc. Such cleaning products typically include at least one other substance to promote cleaning, e.g. NaOH, borax, surfactants, chelating agents, etc.

The IA liquids and products described herein may be used as bulk liquids, or, alternatively, may be utilized or applied as mists or sprays.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

EXAMPLES

Example 1

Calculating Ionization Energy

Gibbs energy, G, is a measure of how much energy, in kJ, a system has available to use. Under standard conditions, Gibbs energy is denoted by G°. G° is the thermodynamic connection between standard reduction potential and spontaneity of a reaction. In the equation $$\Delta G° = -nFE°$$

n is the number of moles of electrons transferred,
F is Faraday's constant=96485 C/mol e−, and
E° is the standard reduction potential for a given reaction.
The Gibbs Energy Equation can be used to calculate ionization energies for a reaction of purified water with ID metal/mineral blends such as that shown below and thus to predict the long term stability of the alkaline water solution. For example, if the Gibb's energy value is highly negative then the solution will be very reactive and the stability will be short-term. If the Gibbs energy value is slightly negative to slightly positive, the solution will be very stable. Finally, if the Gibbs Energy value is very positive, there will be no reaction at all. In the exemplary metal/mineral blend shown below, the Gibbs Energy Value is −231.5 kJ.

Densified (pure) Magnesium—45%
Calcium Magnesium Alloy 5%
Ferro-Silicon—20%
Calcium-Silicon—10%
Zinc Flake—10%
Copper—5%
Calcium carbonate—5%

This blend/combination produces a mildly reactive reducing environment and ionizes water ($H_2O$) molecules into (H+) hydrogen and (OH—) hydroxyl ions without excess energy. Thus, donated and acquired electrons are not highly reactive and the resulting solution exhibits long-term stability.

Example 2

Pet Watering Bowls

Most pet owners put out fresh water for their animals one to three times per day. If the pet owner wanted to give their animal ionized alkaline water, the hydration properties would quickly dissipate in the bowl because it is exposed to air which causes the water to oxidize and lose its beneficial properties.

A pet watering bowl is designed with a perforated drinking section (e.g. like a colander) and in which the space between the bottom of the bowl and the perforated drinking section is filled with Ion Dispersion media. This design enables the water to be in constant contact with the ID media without the pet having access to or being exposed to the media. Having the pet's water continually in contact with the ID media prevents the ionized water from losing its beneficial properties because it is continually ionizing, even as the air is oxidizing the water.

Example 3

Exemplary Products made with ID Water, Expressed as Weight %

The following exemplary product formulations are contemplated. Ingredients amounts are expressed as weight %.

i) Animal Wound Care Hydrogel

| | |
|---|---|
| Tea Tree Oil | 1% |
| Clove Oil | 1% |
| Salicylic Acid | 0.5% |
| Lubrizol CARBOPOL ® 980 Polymer | 0.5% |
| ID Alkaline Water | 97% |

To a clean sterile container, add ID alkaline water and begin mixing vigorously. Add CARBOPOL® gelling agent and mix until CARBOPOL® is completely dissolved. Add White Willow Bark, Tea Tree Oil and Clove Oil and continue mixing. Note: the solution will thicken slightly. Neutralize the product with an 18% solution of NaOH. It will take about 0.025% of the NaOH solution.

ii) Animal Wound Care Liquid Spray

| | |
|---|---|
| Tea Tree Oil | 1% |
| Clove Oil | 1% |
| White Willow Bark | 3% |
| Lubrizol CARBOPOL ® 676 Polymer | 0.3% |
| ID Alkaline Water | 94.7% |

To a clean sterile container, add ID alkaline water and begin mixing vigorously. Add CARBOPOL® gelling agent and mix until CARBOPOL® is completely dissolved. Add White Willow Bark, Tea Tree Oil and Clove Oil and continue mixing. Note: the solution will thicken slightly. Do not neutralize.

iii) Multi-Surface Cleaning Formula

| | |
|---|---|
| Sodium Hydroxide | .25% |
| Sodium Coco Sulfate (30%) | 5% |
| Dow VERSENE ™ (EDTA-based chelating agent) | 2% |
| DOWFAX ™ 8390 (surfactant) | 3% |
| Tea Tree Essential Oil | 1.5% |
| Clove Essential Oil | 1% |
| Lemon Essential Oil | 0.5% |
| Thyme Essential Oil | 2% |
| ID Alkaline Water | 84.75% |

Add ID Alkaline Water to a clean mixing tank. Turn mixer on a medium speed creating a vortex. Add the ingredients in the following order: sodium hydroxide, VERSENE™, the essential oils then the DOWFAX™ 8390. Mix for 15 minutes iv) De-Scaling Solution (e.g. for Use in Removing Scale in Ice Machines)

| | |
|---|---|
| ID Alkaline Water | 93.26% |
| Hydrogen Chloride | 2.64% |
| Dow VERSENE ™ | 0.3% |
| DOWFAX ™ 8390 | 3.8% | vi) Grill & Griddle Cleaner

| | |
|---|---|
| Dow VERSENE™ | 5% |
| Borax (5 moles) | 1% |
| DOWFAX™ 8390 | 2% |
| Sodium Hydroxide | 5% |
| ID Alkaline Water | 87% |

Add IDT water to a clean sterile tank. Add Sodium Hydroxide, VERSENE™ and Borax in this order. Mix for 5 minutes or until all powders are dissolved. Add DOW-FAX™ 8390 and mix for an additional 3 to 5 minutes. Note: Run mixer at low speed to keep product from foaming.

vii) Wine and Cocktail Glass Cleaner

| | |
|---|---|
| ID Water | 95.75% |
| Dow VERSENE™ | 2% |
| Borax (5 moles) | 1% |
| DOWFAX™ 8390 | 1% |
| Sodium Hydroxide | .25% | viii) Floor Cleaner

| | |
|---|---|
| Dow VERSENE™ | 5% |
| Borax (5 moles) | 2% |
| Sodium Hydroxide | 2% |
| DOWFAX™ 8390 | 2% |
| IDT Alkaline Water | 89% |

Add IDT water to a clean sterile tank. Add sodium hydroxide, VERSENE™ and borax in this order. Mix for 5 minutes or until all powders are dissolved. Add DowFax 8390 and mix for an additional 3 to 5 minutes. Note: Run mixer at low speed to keep product from foaming.

ix) Leather Cleaner

| | |
|---|---|
| DOWFAX™ 8390 | 1% |
| Dow VERSENE™ | 1.5% |
| Citric Acid | 2% |
| Grapefruit Seed Oil | 1% |
| Thymol (2-isopropyl-5-methylphenol, IPMP) | 0.5% |
| ID Alkaline Water | 94% | x) Vinyl Cleaner

| | |
|---|---|
| Sodium Hydroxide | 0.25% |
| Dow VERSENE™ | 1% |
| Borax | 0.5% |
| Sodium Bicarbonate | 2% |
| DOWFAX™ 8390 | 1% |
| IDT Water | 95.25% | xi) Boat Wash

| | |
|---|---|
| IDT Water | 94.75% |
| Hydrogen Chloride | 2.25% |
| Dow VERSENE™ | 0.5% |
| DOWFAX™ 8390 | 2.5% | xiv) Moisturizing Aftercare Formula

| | |
|---|---|
| Fulvic acid | 80% |
| ID Water | 20% |

Adjust mixer to medium speed. Add Fulvic acid and mix at medium speed for 2 minutes. Add ingredient ID water and mix at medium speed for 5 minutes. Final product will be slightly amber. Distribute into appropriate containers.

xv) Psoriasis Lotion

| | |
|---|---|
| Phase A: | |
| ID Alkaline water | 70% |
| Glycerin | 4% |
| Stearic acid thickener | 3% |
| Emulsifying Wax | 4% |
| White Willow Bark | 1% |
| Phase B: | |
| Hemp Oil | 10% |
| Shea Oil | 2% |
| Phase C: | |
| *Arnica* Extract | 1% |
| *Calendula* Oil | 1% |
| Horse Chestnut Extract | 1% |
| Spearmint Essential Oil | 2% |
| Germail Preservative | 1% |

In a clean sterile mixing container add ingredients in Phase A then heat to 160° F. Mix Phase A until ingredients melt then add the Phase B oils. Mix at 160° F. for at least 10 minutes. Cool to 130° F. After reaching 130° F., add the ingredients in Phase C and continue mixing allowing the lotion to reach ambient temperature. Note: as product cools it will thicken.

xvi) Acne Formula

| | |
|---|---|
| Tea Tree Oil | 1% |
| Salicylic Acid | 1% |
| Lubrizol CARBOPOL® 980 Polymer | 0.5% |
| ID Alkaline Water | 97.5% |

Mix ID water and CARBOPOL® at high shear speed until dissolved (approx. 10 minutes). Reduce mixer speed so that solution is creating small vortex. Add Willow Bark and essential oils. Mix for 3 to 5 minutes. Neutralize the solution with an 18% sodium hydroxide solution. As pH increases above 6.5 it will form a thick gel. Increase mixer speed to ensure uniform viscosity.

xvii) Alcohol Free Hand Sanitizer

| | |
|---|---|
| ID Alkaline Water | 96.62% |
| Thymol | 0.5% |
| Essential Oil as fragrance | 0.5% |
| *Calendula* Oil | 1.5% |
| Lubrizol CARBOPOL® 980 | 0.5% |
| Benzalkonium Chloride | 0.13% |
| Adjust Viscosity with 18% NaOH | 0.25% | solution after all ingredients are mixed.

xviii) Wound Care and Wound Protectant

| | |
|---|---|
| IDT Alkaline Water | 97% |
| Tea Tree Oil | 1% |

-continued

| | |
|---|---|
| Clove Oil | 1% |
| Salicylic Acid | 0.5% |
| Lubrizol CARBOPOL ® 676 | 0.5% | xix) Anti-Fungal Spray

| | |
|---|---|
| ID Alkaline Water | 98.12% |
| Camphor | 0.5% |
| *Eucalyptus* Essential Oil | 0.5% |
| Menthol | 0.25% |
| NaOH | 0.5% |
| Benzylkonium Chloride | 0.13% | xx) Hand and Body Lotion

| | |
|---|---|
| IDT Alkaline Water | 71% |
| Glycerin | 4% |
| Stearic Acid Thickener | 3% |
| Emulsifying Wax | 4% |
| Avocado Oil | 10% |
| Shea Oil | 2% |
| *Arnica* Extract | 1% |
| *Calendula* Oil | 1% |
| Horse Chestnut Extract | 1% |
| Fragrance Essential Oil (Spearmint) | 2% |
| Germail Preservative | 1% | xxi) Neuropathy Lotion

| | |
|---|---|
| IDT Alkaline Water | 68.75% |
| Glycerin | 4% |
| Stearic Acid Thickener | 4% |
| Emulsifying Wax | 5% |
| Hemp Oil | 8% |
| Shea Oil | 2% |
| Menthol Crystals | 3% |
| Black Pepper Essential Oil | 0.25% |
| Rosemary Essential Oil | 1% |
| *Geranium* Essential Oil | 1% |
| Peppermint Essential Oil | 2% |
| Germail Preservative | 1% | xxii) Shingles Spray Gel

| | |
|---|---|
| IDT Alkaline Water | 23.5% |
| *Aloe Vera* Juice | 59% |
| Guar Gum | 0.5% |
| Glycerin | 4.5% |
| Tea Tree Essential Oil | 3.0% |
| *Eucalyptus* Essential Oil | 3.0% |
| Lavender Essential Oil | 3.5% |
| *Ravensara* Essential Oil | 2.0% | xxiii) Antibacterial Hand Soap

| | |
|---|---|
| ID Alkaline Water | 75.5% |
| Guar Gum | 1% |
| Cocamidopropyl Betaine (35%) | 10% |
| Sodium-Coco-Sulfate | 10% |
| Thymol | 1% |
| Peppermint Essential Oil | 1% |
| *Calendula* Oil | 1.5% | xxiv) Acne Face Wash

| | |
|---|---|
| Tea Tree Oil | 1% |
| Salicylic Acid | 1% |
| Lubrizol CARBOPOL ® 980 Polymer | 0.5% |
| ID Alkaline Water | 97.5% |

Mix IDT Water and CARBOPOL® at high shear speed until dissolved (approx. 10 minutes). Reduce mixer speed so that solution is creating small vortex. Add Willow Bark and essential oils. Mix for 3 to 5 minutes. Neutralize the solution with an 18% sodium hydroxide solution. As pH increases above 6.5 it will form a thick gel. Increase mixer speed to ensure uniform viscosity.

xxv) Air Sanitizer Gel

| | |
|---|---|
| Propylene Glycol | 5.0% |
| Tea Tree Oil | 1.0% |
| Clove Bud Oil | 1.0% |
| Cinnamon Oil | 1.0% |
| Lubrizol CARBOPOL ® 676 Polymer | 0.5% |
| ID Alkaline Water | 91.5% |

Mix IDT Water and CARBOPOL® at high shear speed until dissolved (approx. 10 minutes). Reduce mixer speed so that solution is creating small vortex. Add propylene glycol and essential oils. Mix for 3 to 5 minutes. Neutralize the solution with an 18% Sodium Hydroxide solution. As pH increases above 6.5 it will form a thick gel. Increase mixer speed to ensure uniform viscosity.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A method of producing an ionized alkaline liquid, comprising
   contacting an ionic liquid with a medium comprising:
      about 30-70% by volume of one or more group II elements;
      about 10-20% by volume of one or more rare earth minerals;
      about 1-50% by volume of one or more metal reducing agents; and
      about 1-25% by volume of one or more mineral buffers;
   wherein said step of contacting is carried out for a period of time sufficient to ionize ionizable molecules in said ionic liquid.

2. The method of claim 1, wherein said medium comprises:
   about 50% by volume of one or more group II elements;
   about 15% by volume of one or more rare earth minerals;
   about 30% by volume of one or more metal reducing agents; and
   about 5% by volume of one or more mineral buffers.

3. The method of claim 1, wherein said step of contacting is carried out by flowing said ionic liquid through said medium.

4. The method of claim 1, wherein said step of contacting is carried out by static exposure of said ionic liquid to said medium.

* * * * *